US006419675B1

(12) United States Patent
Gallo, Sr.

(10) Patent No.: US 6,419,675 B1
(45) Date of Patent: Jul. 16, 2002

(54) ELECTROSURGICAL COAGULATING AND CUTTING INSTRUMENT

(75) Inventor: David P. Gallo, Sr., New Hartford, NY (US)

(73) Assignee: ConMed Corporation, Utica, NY (US)

( * ) Notice: Subject to any disclaimer, the term of this patent is extended or adjusted under 35 U.S.C. 154(b) by 0 days.

(21) Appl. No.: 09/390,087

(22) Filed: Sep. 3, 1999

(51) Int. Cl.[7] ............................................... A61B 18/18
(52) U.S. Cl. ........................... 606/46; 606/45; 606/205; 606/207
(58) Field of Search ..................... 606/45, 46, 171, 606/205, 206, 207, 210

(56) References Cited

U.S. PATENT DOCUMENTS

| | | |
|---|---|---|
| 2,068,721 A | 1/1937 | Wappler et al. |
| 4,003,380 A | 1/1977 | Wien .................... 128/303.17 |
| 4,611,595 A | 9/1986 | Klieman et al. ......... 128/334 R |
| 5,147,378 A | 9/1992 | Markham .................. 606/206 |
| 5,207,691 A | 5/1993 | Nardella ................... 606/142 |
| 5,222,973 A | 6/1993 | Sharpe et al. ............. 606/206 |
| 5,258,006 A | 11/1993 | Rydell et al. ............. 606/205 |
| 5,318,589 A | 6/1994 | Lichtman ................. 606/205 |
| 5,383,888 A * | 1/1995 | Zvenyatsky et al. ....... 606/206 |
| 5,443,463 A | 8/1995 | Stern et al. .................. 606/51 |
| 5,445,638 A | 8/1995 | Rydell et al. ............... 606/51 |
| 5,458,598 A | 10/1995 | Feinberg et al. ........... 606/52 |
| 5,476,479 A | 12/1995 | Green et al. .............. 606/205 |
| 5,483,952 A | 1/1996 | Aranyi ..................... 600/131 |
| 5,499,997 A | 3/1996 | Sharpe et al. ............. 606/206 |
| 5,527,313 A | 6/1996 | Scott et al. ................. 606/51 |
| 5,562,655 A | 10/1996 | Mittelstadt et al. ........... 606/1 |
| 5,584,845 A * | 12/1996 | Hart ......................... 606/174 |
| 5,620,459 A | 4/1997 | Lichtman ................. 606/205 |
| 5,665,100 A | 9/1997 | Yoon ....................... 606/170 |
| 5,735,849 A | 4/1998 | Baden et al. ................ 606/51 |
| 5,800,449 A | 9/1998 | Wales ...................... 606/172 |
| 5,868,785 A | 2/1999 | Tai et al. .................. 606/207 |

FOREIGN PATENT DOCUMENTS

| | | |
|---|---|---|
| DE | 296 16 065 U | 1/1998 |
| EP | 0 517 243 A | 12/1992 |
| EP | 0 741 996 A | 11/1996 |
| WO | WO 97/05829 | 2/1997 |

* cited by examiner

*Primary Examiner*—Linda C. M. Dvorak
*Assistant Examiner*—R. Kearney

(57) ABSTRACT

An electrosurgical coagulating and cutting instrument employing pairs of clamping arms having wrist portions proximal to closing ramps and jaws and configured to close at their wrists first, then their distal tips and lastly, their heels. The instrument includes mechanisms for preventing the advancement of a cutting blade when the jaws are not closed. An actuator for closing the jaws includes an actuator handle and a drive head having teeth formed therein and a pawl mounted in the handle for engaging the teeth, these latter structures forming a ratcheting mechanism. Said mechanism is controllably releaseable.

12 Claims, 10 Drawing Sheets

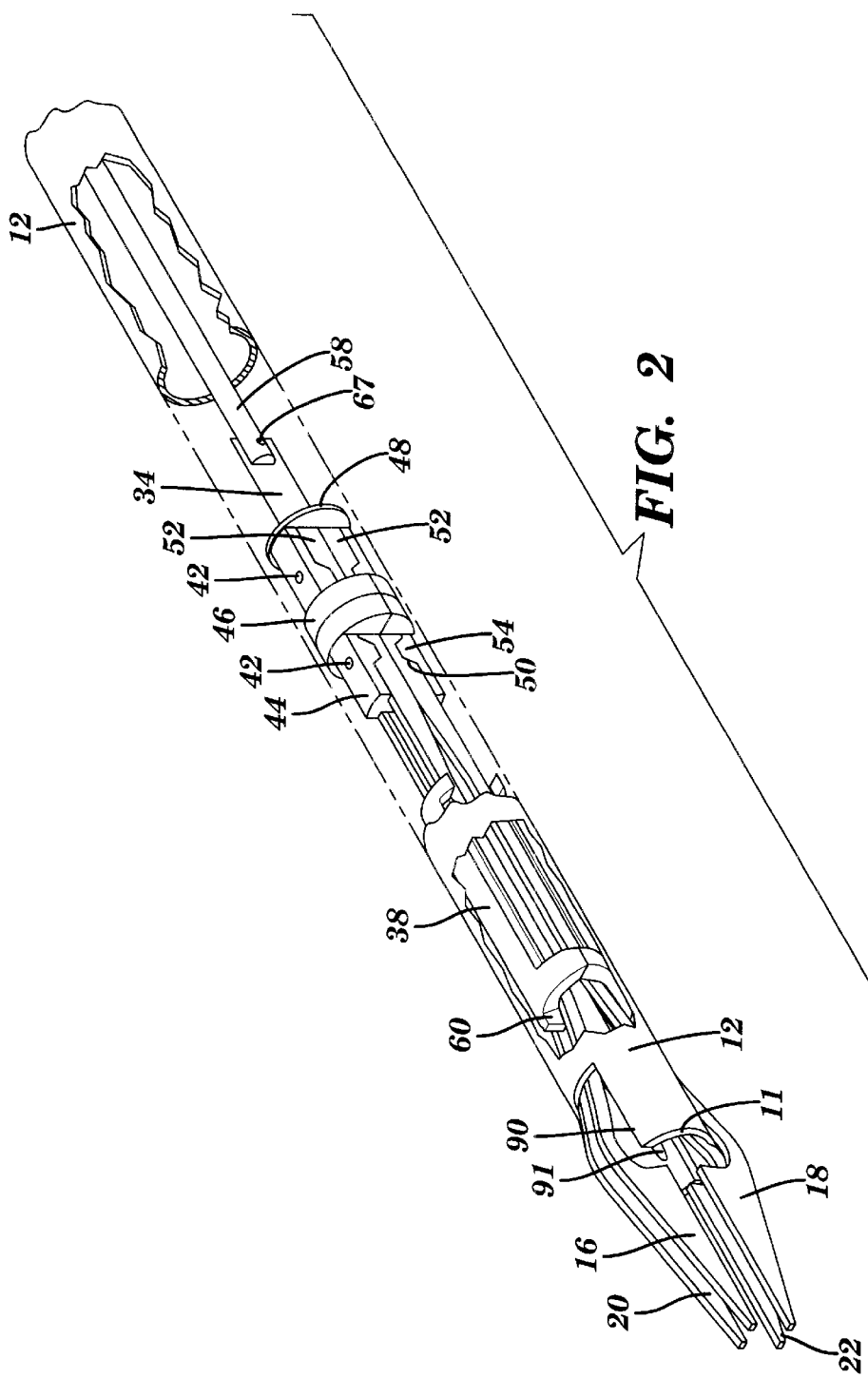

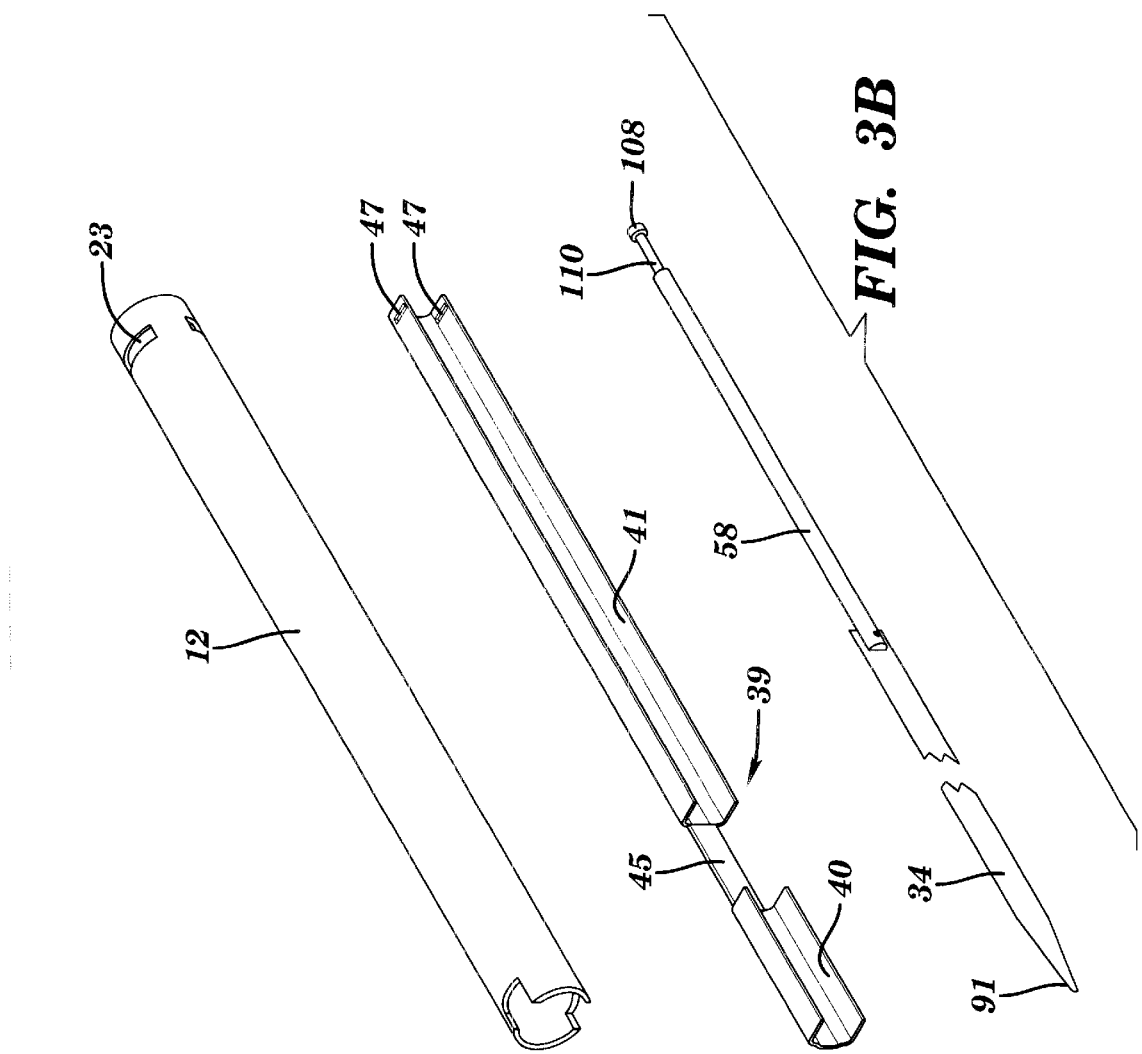

ELECTROSURGICAL COAGULATING AND CUTTING INSTRUMENT

BACKGROUND AND SUMMARY OF THE INVENTION

This invention relates to endoscopic surgery and, in particular, to an improved electrosurgical coagulating and cutting instrument.

There are a number of endoscopic instruments having movable jaws formed at the distal ends of clamping arms which diverge distally. Closure is typically effected by distally advancing a collar or other component over the diverging arms so as to urge the arms and jaws together. Examples of such devices are found in U.S. Pat. Nos. 5,258,006 ; 5,445,638 ; 5,527,313 and 5,735,849. Relatively few of these devices close at their tips before fully grasping target tissue, thus making it difficult to capture such tissue. Furthermore, the maximum width of the opening between the jaws tends to be limited by the diameter of the tubular sheath housing the movable components of such instruments. Another shortcoming of the prior art involves unnecessarily complicated ratcheting mechanisms for preventing the opening of jaws once closed. Such mechanisms often provide for only coarse incremental ratcheting of the closure movements to the jaws. Yet another shortcoming of prior art devices is that those containing cutting elements lack sufficient protection against unintended advancing of the cutter when the jaws are open, thereby creating the danger of unintentionally lacerating tissue in the vicinity of the jaws. Also, many prior art devices are not configured to prevent the cutter from protruding outside the limits of the jaw envelope when the jaws are closed. Again, this shortcoming results in the danger of causing unintentional lacerations of tissue in the vicinity of the jaws. The invention described herein addresses these and other shortcomings of the prior art.

SUMMARY OF THE INVENTION

In one aspect, the subject invention is comprised of a tubular sheath having an actuator on its proximal end and movable jaws protruding from its distal end, the jaws being a portion of clamping arms anchored within the sheath, each arm having a ramp proximal to the jaw and a wrist proximal to the ramp. The clamping arms are closed by the distal movement of a drive chassis having camming surfaces at its distal end which engage the ramps so as to urge the arms together, the arms being so configured that, as they are urged together, they meet first at their wrists, then at their distal tips and, lastly, at their heels. In a preferred embodiment of the invention, two pairs of clamping arms with movable jaws are provided and the camming surfaces at the distal end of the drive chassis are formed as distal plug components having lugs extending between the pairs of clamping arms so as to maintain the proper alignment of the arms during use of the instrument.

In another aspect, the subject invention is comprised of a tubular sheath having a handle including a drive head movable between a jaws open position and a jaws closed position, at least one pair of clamping arms, each arm including a jaw, the clamping arms and jaws being movable relative to one another between an open position and a closed position, a drive chassis disposed within the sheath and serving to open and close the jaws in response to movement of the drive head and a ratchet comprising a series of teeth formed on the head and a pawl mounted in the handle for engaging the teeth.

In another aspect, the invention is comprised of a tubular sheath having a handle on its proximal end, including a drive head operable between positions corresponding to the jaws being opened and closed, two pairs of clamping arms in a spaced-apart, parallel relationship, a drive chassis operably positioned between the driving bead and the clamping arms to effect closure of the arms and their associated jaws, a surgical cutter disposed between the pairs of arms, a drive rod operatively coupled to the cutter on its proximal end and operatively associated with a drive plate at its proximal end, the plate being operable to advance the rod and cutter, said plate being disposed proximally adjacent the head so as to be blocked in its movement toward the cutter advanced position when the head is not in its jaws closed position.

In yet another aspect, the invention is comprised of a method of closing the jaws of one or more pairs of clamping arms, the method involving securing relatively elongate clamping arms at their proximal end to the outer sheath of an endoscopic surgical instrument, said arms having jaws at their distal ends, ramps proximal to the jaws and wrists proximal to the ramps. This closure method further involves advancing camming surfaces distally along the ramps so as to urge the arms together, the configuration of the arms being such that they meet first at their wrists, then at the distal tips of the jaws and lastly at the heels of the jaws.

In yet another aspect, the method of this invention involves the use of two pairs of arms having jaws at their distal ends, ramps proximal to the jaws and wrists proximal to the ramps as well as a surgical cutter disposed between the pairs of arms for reciprocating longitudinal movement between an advanced position for cutting tissue between the jaws and a retracted position in which the cutter is proximal to the heels of the jaws. This method further involves urging the jaws together with camming surfaces advanced against the ramps so as to cause the arms to meet first at their wrists, then at the distal tips of the jaws and lastly at the heels of the jaws following which electrosurgical energy is provided to the jaws so as to coagulate tissue captured therein. After coagulation, the cutter is advanced so as to cut tissue captured between the pairs of jaws. During actuation, the appropriate separation and alignment of the jaws may be maintained by the use of lugs disposed between the corresponding arms of adjacent jaw pairs.

In yet another aspect, the invention involves the method of providing for a ratcheted closure sequence in which an actuator handle is used to effect closure, said actuator handle having a drive head with teeth formed thereon for engagement with a pawl. In a preferred method, the pawl is comprised of two tines of unequal length so as to provide for finer ratcheting with teeth of a given size than would otherwise be possible with a single tine or tines of equal length.

BRIEF DESCRIPTION OF THE DRAWINGS

FIG. 2 is an enlarged perspective view of a distal portion of the instrument with parts of the outer sheath broken away.

FIG. 3B is a detailed assembly drawing of selected components depicted in FIG. 3A.

In FIG. 7E, the two jaws closest to the viewer have been removed in order to more clearly show the cutter.

DETAILED DESCRIPTION OF THE DRAWINGS

Figure 1:
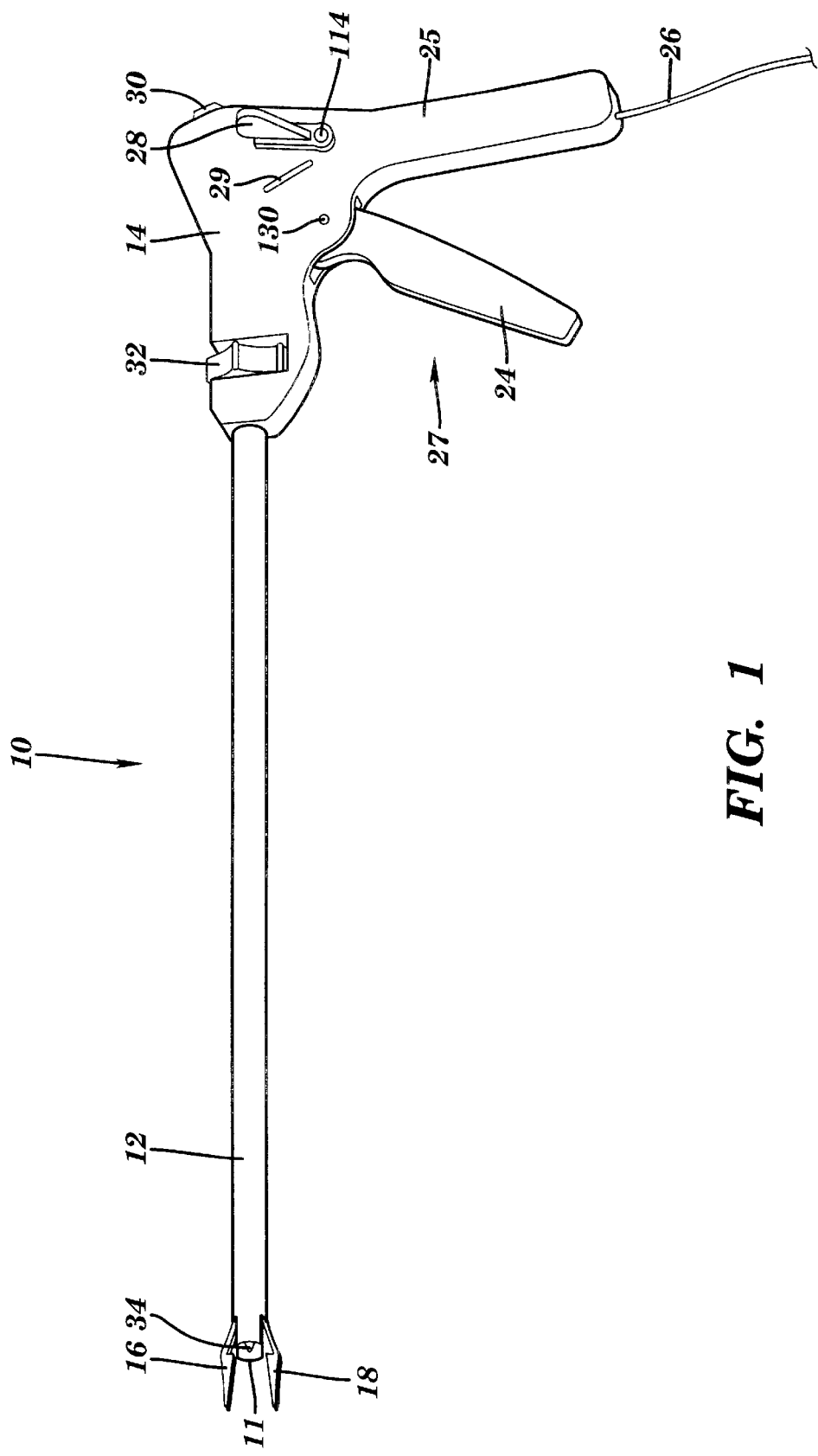
FIG. 1 is a perspective view of an instrument embodying the subject invention.

FIG. 1 shows the general arrangement of a preferred embodiment of the electrosurgical coagulating and cutting instrument 10 of this invention. Tubular sheath 12 extends proximally into handle 14 and has a distal end 11. Jaws 16, 18, 20 and 22 (see FIG. 2) protrude beyond the distal end 11 of sheath 12. Jaws 16, 18, 20 and 22 are electrically isolated and may be connected to an electrosurgical generator by means of cable 26. Mounted on a distal portion of handle 14 is a rotation knob 32 which, as explained below, is used to rotate sheath 12 along with jaws 16, 18, 20 and 22 with respect to handle 14. A jaw actuator 27 is mounted on axle 130 on handle 14. As explained below, when actuator handle 24 is grasped and moved toward stationary grip 25, jaws 16, 18, 20 and 22 will be closed. The closure action of the jaws can be controlled by a ratchet mechanism which, in turn, is selectively engaged or disengaged by moving ratchet control 30 up or down. Ratchet control 30 is conveniently located for operation with the surgeon's thumb.

Also seen in FIG. 1 is the tip of surgical cutter 34. As explained below, cutter 34 may be advanced distally by operation of a cutter advance control in the form of ear 28. A stop 29 is provided to limit the distal movement of blade 34. Again, ear 28 is conveniently placed for operation by the surgeon's thumb. A corresponding ear is desirably placed on the right-hand side of instrument 10 for additional convenience.

Figure 3A:
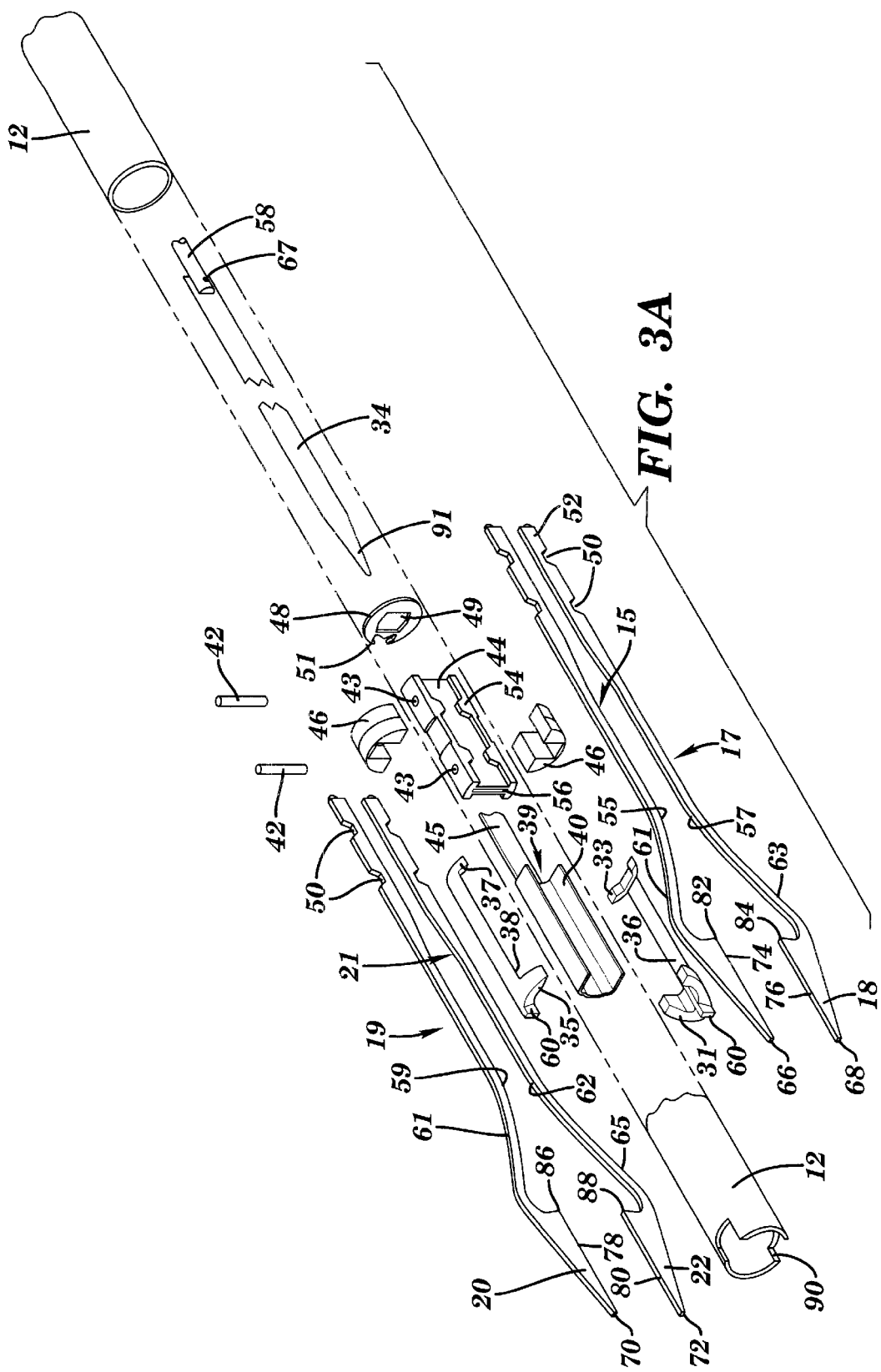
FIG. 3A is an exploded view of the parts shown in FIG. 2.

Referring now to FIGS. 2 and 3A, it will be seen that a preferred embodiment of the invention may include four clamping arms 15, 17, 19 and 21. Arms 15 and 17 constitute a pair arranged in opposed relation to each other. Likewise, arms 19 and 21 constitute another pair in the same relationship. Pair 15, 17 and pair 19, 21 are in a parallel, spaced-apart relationship, as shown in FIG. 2. As also shown in FIG. 2, surgical cutter 34 passes through sheath 12 between clamping arm pairs 15, 17 and 19, 21.

Clamping arms 15, 17, 19 and 21 are secured to sheath 12 by means of an arm anchoring fixture 44 and centering members 46. Sheath 12 is made of any suitably rigid material such as metal or plastic. If made of metal, sheath 12 is preferably spray coated with an insulating material such as a polyurethane to provide electrical isolation between the sheath and the patient's body. Fixture 44 and members 46 are preferably made of a nonconducting material such as a plastic having suitable mechanical properties for their indicated purpose.

Anchoring fixture 44 is secured in sheath 12 by means of pins 42 which pass through sheath 12 and are press-fitted into holes 43 (see FIG. 3A) in fixture 44. Although not shown, similar pins and holes are provided on the underside of the instrument to provide additional security. To prevent longitudinal movement of arms 15, 17, 19 and 21 with respect to sheath 12, the arms are provided with indentations 50 which engage lugs 54 on fixture 44. The proximal ends 52 of arms 15, 17, 19 and 21 are provided with apertures 53 (see FIG. 7A) to facilitate attachment of electrical wires for connection to an electrosurgical unit. An uninsulated or "stripped" end of an insulated wire (not shown) can conveniently be threaded through an aperture 53, twisted around itself, soldered and then covered with a shrink-wrapped insulating material. It is important that the wires connected to ends 52 be kept electrically isolated from one another so as to prevent shorting between themselves or with other components of the instrument. Other methods of wire attachment may be used. For example, it would be possible to create a pin and socket arrangement in which ends 52 would be formed as pins and sockets would be fixed to the ends of the wires.

Referring again to FIGS. 2 and 3A, clamping arms 15, 17, 19, and 21 are electrically isolated from one another by means of an insulating coating (not shown) such as a thin layer of polyurethane. Such a coating may be applied by any conventional process such as spray coating. Tissue grasping surfaces 74, 76, 78 and 80 (see FIG. 3A) of arms 15, 17, 19 and 21 are not coated, however. This permits these surfaces to grasp tissue and to transmit electrosurgical energy through such tissue for coagulation purposes.

Also shown in FIGS. 2 and 3A is a plastic sealing disk 48 having a central opening 49 and a side opening 51. Disk 48 is intended to prevent the passage of gas or fluids from the distal end of the instrument through sheath 12. Disk 48 is thus sized to be in intimate contact with the interior of sheath 12. Central opening 49 matches the cross-sectional shape of anchoring fixture 44, thus allowing disk 48 to be tightly fit on the proximal end of fixture 44. Disk 48 is also provided with a side opening 51 through which the spine 45 of drive chassis 39 may pass, as explained below.

Figure 4:
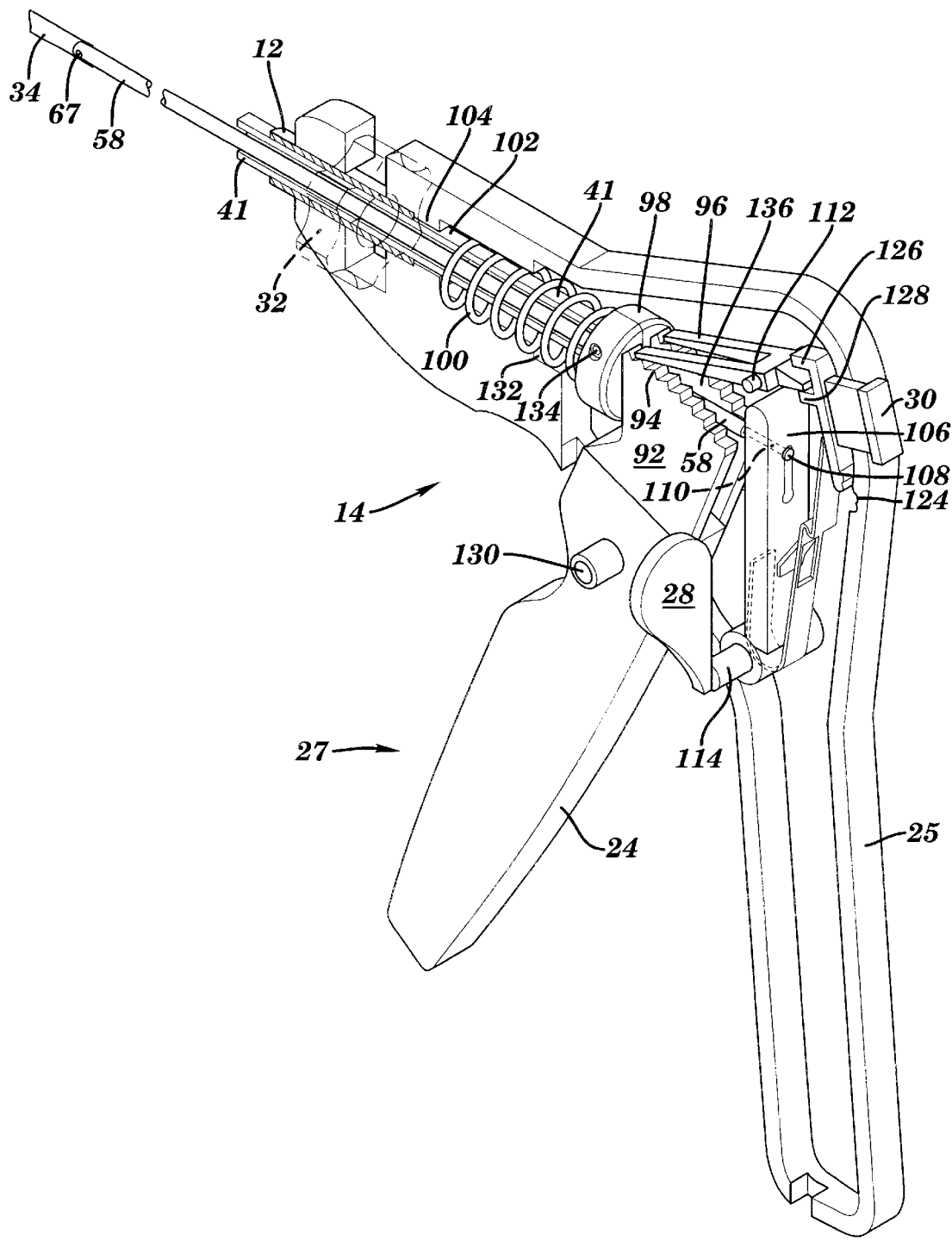
FIG. 4 is a perspective view of the handle of an instrument embodying the invention, partly in section, with the left side of the housing removed.

FIG. 3B shows the manner in which sheath 12, drive chassis 39, drive rod 58 and cutter 34 are assembled. Drive chassis 39 is made of stainless steel and is comprised of a spine 45 running the full length of the chassis. Chassis 39 has two "C" channels, distal "C" channel 40 and proximal "C" channel 41. Drive chassis 39 is spray coated in its entirety with a polyurethane material having high dielectric strength and good wear resistance. This material may be the same as that used to coat the clamping arms 15, 17, 19 and 21 and sheath 12. Slots 47 are provided near the proximal end of "C" channel 41 to facilitate attachment of drive collar 98 shown in FIGS. 4, 5 and 6. As best seen in FIG. 4, proximal "C" channel 41 extends into handle 14. Drive collar 98 is rigidly attached to the proximal end of "C" channel 41. To facilitate this attachment, drive collar 98 is formed in two halves which together surround the proximal end of "C" channel 41. Each of the halves is formed with a rib (not shown) on its inside surface to engage slot 47 of "C" channel 41 (see FIG. 3B). The two halves of drive collar 98 may be held together by means of screws 134 or any other suitable method of attachment. For example, another method of attachment, and one which is preferred, is to form the two halves of drive collar 98 with mating pins and recesses sized so that they will engage each other in a frictional fit as they are assembled about the proximal end of "C" channel 41.

Figure 5:
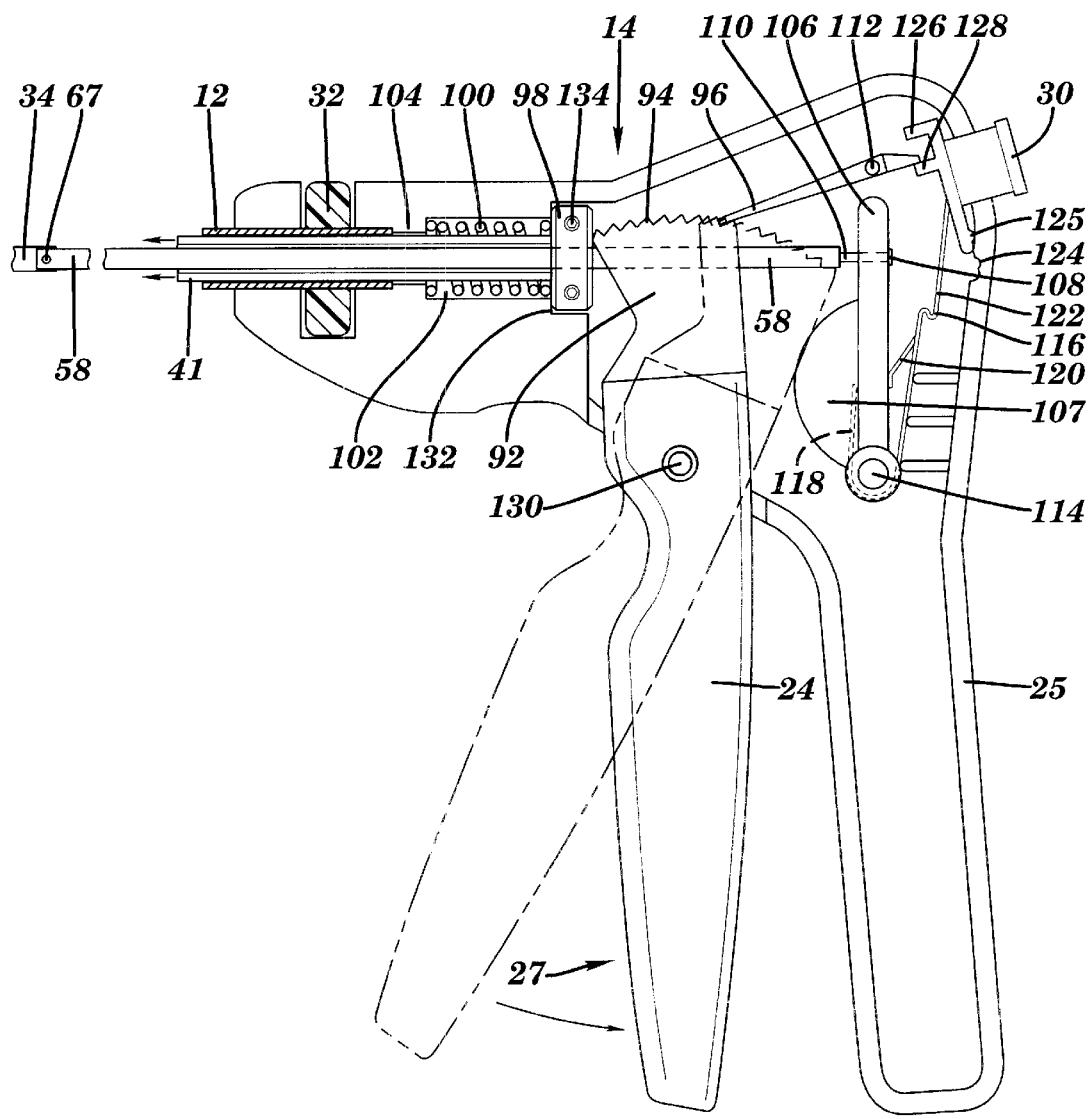
FIGS. 5 and 6 are left-side elevations with the left side of the housing removed, partly in section, showing the operation of certain components contained within the handle of the instrument.

Referring again to FIG. 3B, it will be understood that in the assembled instrument, drive chassis 39 is disposed within sheath 12. Also, it will be appreciated that in the assembled instrument, drive rod 58 passes through proximal "C" channel 41 and, as shown in FIGS. 4 and 5, extends proximally into handle 14 where shank 110 and button 108 cooperate with drive plate 106 in a manner described below. Drive rod 58 may be made of any suitable material such as metal or plastic.

As shown in FIG. 2, cutter 34 is of sufficient length to pass from its cutting edge 91 at the distal end of the instrument proximally between the clamping arm pairs 15, 17 and 19, 21 and through a slot 56 (see FIG. 3A) in fixture 44 and seal 48 after which it is attached by means of a pin-type component 67 to drive rod 58. In FIG. 2, cutter 34 is shown in its retracted position. The distance from disk 48 to the distal end of drive rod 58 must be sufficient to accommodate the movement of cutter 34 to its advanced position. Also, the distance between distal "C" channel 40 and proximal "C" channel 41 (see FIG. 3B) must be sufficient on either end of fixture 44 to accommodate the reciprocal movement of drive chassis 39 between its jaws open position and its jaws closed position. Cutter 34 is preferably made of stainless steel with a sharpened cutting edge 91.

Referring again to FIGS. 2 and 3A, it will be seen that, in a preferred embodiment of the invention, a pair of distal plugs 36 and 38 are assembled over distal "C" channel 40. Plug 36 contains at its ends semi-circular centering collars 31 and 33. Similarly, plug 38 is formed with collars 35 and 37. Collars 31 and 35 are formed with separation lugs 60. As seen in FIGS. 2 and 3A, the separation lugs 60 serve to maintain the separation between the clamping arms of pairs 15, 17 and 19, 21 during activation. In other words, the separation of the two top clamping arms 15 and 19 is maintained by lug 60 on plug 38 while the separation between the bottom clamping arms 17 and 21 (see FIG. 3A) is maintained by lug 60 on plug 36. Besides serving to keep the clamping arms centered within sheath 12, plugs 36, 38 serve on their distal ends to cam the clamping arms 15, 17, 19, and 21 together as the drive chassis 39 moves distally. In this regard, it will be seen in FIG. 3A that clamping arms 15 and 17 include ramps 61 and 63, respectively. Similarly, clamping arms 19 and 21 include ramps 64 and 65. Semi-circular collars 31 and 35 (see FIG. 3A) engage these ramps as drive chassis 39 moves distally. Although the instrument will function without the plugs 36,38, it is preferable to include them.

Figure 6:
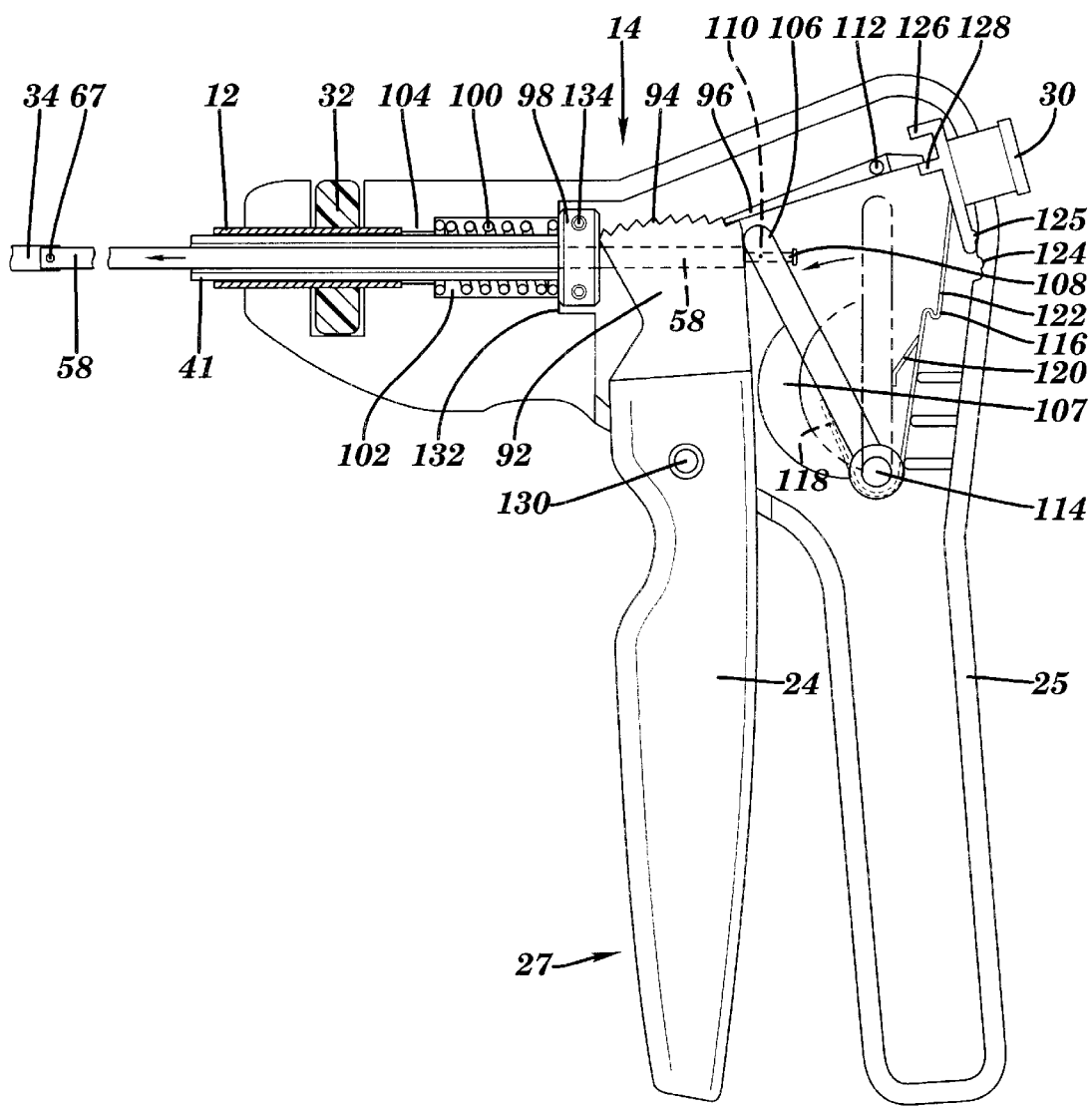

FIGS. 4, 5 and 6 illustrate the mechanisms and structures used to advance and retract the drive chassis, thus closing and opening jaws 16, 18, 20 and 22. Actuator 27 is a plastic lever pivotally mounted on axle 130. Axle 130 is molded as a part of actuator 27 and the right and left sides of the housings of handle 14, also plastic, are molded with a suitable aperture into which axle 130 rotatably fits. The upper portion of actuator 27 is formed as a drive head 92 positioned adjacent chassis drive collar 98. Spring 100 biases the drive chassis proximally to its jaws open position. When actuator handle 24 is drawn toward stationary grip 25, drive head 92 moves distally forcing collar 98 and drive chassis 39 to move distally. As that occurs, the centering collars 31 and 35 found on the distal ends of plugs 36 and 38 (see FIG. 3A) engage ramps 61, 63, 64 and 65 so as to urge the clamping arms together. One of the lugs 60 (see FIGS. 2 and 3A) is disposed between ramps 61 and 64 while the other is disposed between ramps 63 and 65, thus serving to keep the clamping arms properly aligned and separated during activation.

Spring 100 is disposed within cavity 102 against shoulder 104 and against drive collar 98. Thus, as actuator handle 24 is operated to its jaws closed position, spring 100 is compressed. When the actuator handle is released (and pawl 96 is disengaged from teeth 94 as explained below), spring 100 will drive collar 98 and drive chassis 39 proximally, thus allowing jaw pairs 16, 18 and 20, 22 to resume their open position.

Figure 7A:
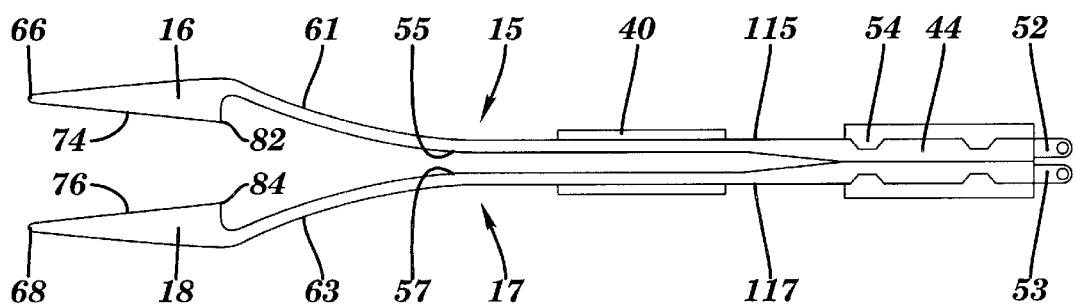
FIGS. 7A–E are a series of side elevations showing the closure sequence of the clamping arms and their jaws as well as the movement of the cutter of the instrument.

The closure sequence is illustrated in FIGS. 7A–E. For the sake of simplicity, the distal plugs 36 and 38 are not shown. FIG. 7A shows jaws 16 and 18 in their open position. As shown in FIGS. 7A and 3A, clamping arm 15 terminates in a jaw member 16 which includes a distal tip 66 and a heel 82 separated by a tissue grasping surface 74. Proximal to jaw 16 is ramp 61. Proximal to ramp 61 is wrist 55. Wrist 55 is located where clamping arm 15 begins to diverge distally from clamping arm 17. The portion of clamping arm 15 proximal to wrist 55 is substantially straight until the arm begins to thicken near its proximal end 52. Clamping arm 19 is identical in configuration to clamping arm 15. Clamping arms 17 and 21 are identical in configuration but are disposed in opposed relation to clamping arms 15 and 19, respectively.

Figure 7B:
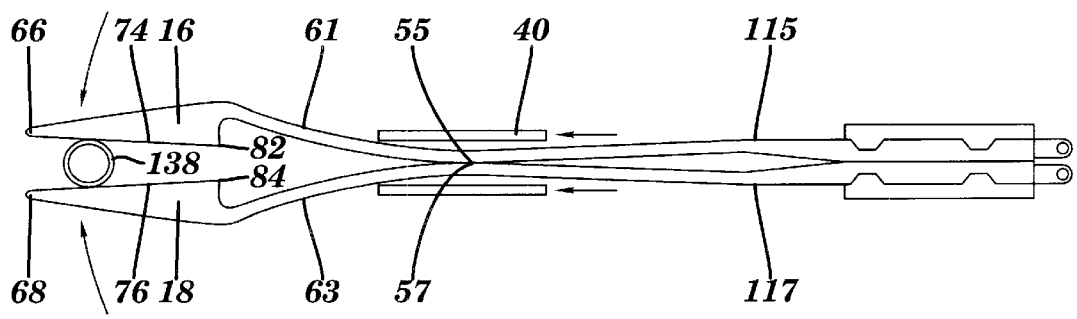
Figure 7C:
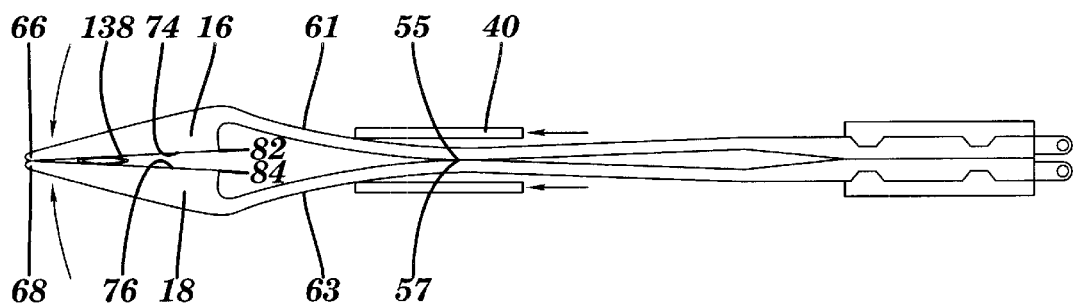
Figure 7D:
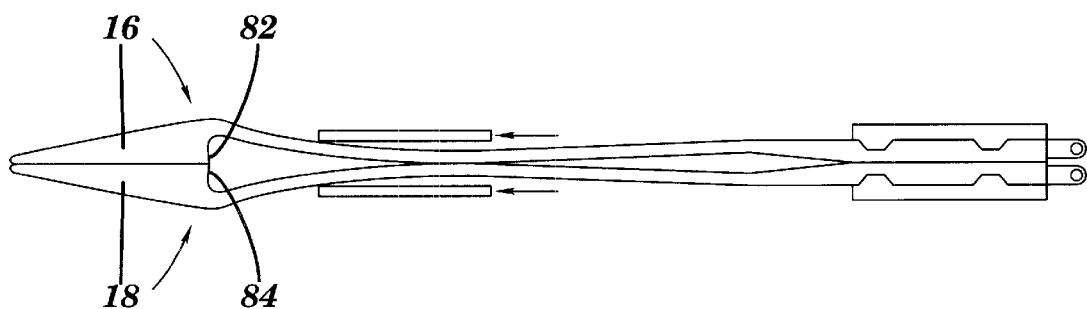

FIG. 7B illustrates that as "C" section 40 of drive chassis 39 moves distally along ramps 61 and 63, the clamping arms are urged toward one another and first meet at their wrists 55 and 57. This occurs because the clamping arms 15 and 17 are cross-sectionally shaped so that they will bend at flex points 115 and 117, respectively. In FIG. 7B, a blood vessel 138 has been captured loosely between jaws 16 and 18. The next step in the closing sequence is illustrated in FIG. 7C. There, the drive chassis has been further advanced distally causing tips 66 and 68 to meet. Note that heels 82 and 84 are still spaced apart. In FIG. 7D, it is seen that further distal advancement of the drive chassis results in bringing heels 82 and 84 together, thus completing the closure of jaws 16 and 18.

Figure 7E:
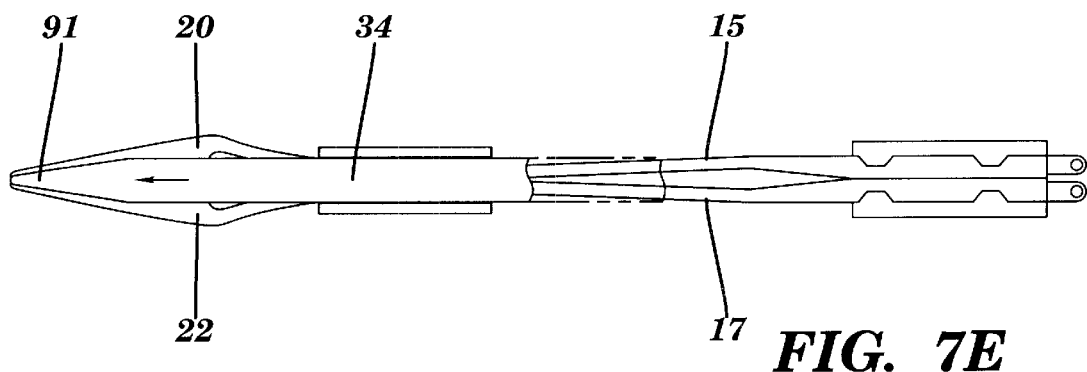

Once closure has been completed, the jaws can be supplied with electrosurgical energy to coagulate the tissue between them. The bipolar coagulation process is generally known and for most applications, jaws 16 and 20 (see FIG. 3A) are of one polarity while jaws 18 and 22 are of the other. After coagulation has occurred, cutter 34 is advanced to cut the captured tissue. It will be appreciated that cutter 34 passes between jaw pairs 16, 18 and 20, 22. As shown in FIG. 7E (in which jaws 16 and 18 have been removed), cutter 34 may be advanced to a point where its distal tip is substantially aligned with the distal tips of jaws 16, 18, 20 and 22. In the preferred embodiment of this instrument, cutter 34 is configured so as to prevent its cutting edge 91 or any other part of cutter 34 from protruding outside the envelope of space defined by and between jaw pairs 16, 18 and 20, 22.

It may be noted that drive head 92 is slotted, as shown in FIG. 4 to accommodate the passage of cutter drive rod 58. Also, drive head 92 is provided with teeth positioned for interaction with pawl 96. Pawl 96 is made of a molded plastic with an integral axle 112. Suitable recesses (not shown) are provided in both halves of handle 14 to receive axle 112, thus permitting movement of pawl 96 into or out of engagement with teeth 94. Ratchet control 30 (see FIG. 5) engages pawl 96 with its lips 126, 128. Ratchet control 30 is urged proximally by spring 122 against the housing of handle 14. Detent recess 124 is engaged by detent lug 125 when the ratchet control 30 is moved to its lower position. In that position, lip 126 rotates pawl 96 about axle 112, thereby disengaging pawl 96 from teeth 94. When pawl 96 is disengaged, actuator handle 24 may be freely drawn to stationary grip 25 and released as desired, thus permitting drive chassis 39 to move reciprocally opening and closing jaws 16, 18, 20 and 22. When the pawl is engaged, as shown in FIGS. 4–6, actuator handle 24 will not return to its jaws open position. Thus, if the ratchet control 30 is in its upper position, drive head may not move proximally after it has been moved distally. As seen in FIG. 4, pawl 96 is comprised of a pair of tines. One tine is shorter than the other so that they may alternately engage teeth 94 in a stepwise fashion. This arrangement provides for finer increments in the ratcheting operation then would be the case if the tines were of equal length.

FIGS. 4, 5 and 6 also illustrate the structures and methods by which cutter 34 is advanced. As noted earlier, drive rod 58 extends through "C" channel 41, drive collar 98, drive head 92 and is engaged with cutter drive plate 106. Formed in plastic, cutter drive plate 106 is integral with axle 114 which, in turn, is driven by ear 28. Ear 28 is rigidly fixed to axle 114 and, thus, as ear 28 is rotated counter clockwise about axle 114, plate 106 is rotated correspondingly. As plate 106 advances, it forces cutter drive rod 58 distally, thus advancing cutter 34. Note that shank 110 is slideably fit within the vertical slot 109 (see FIG. 4) of drive plate 106. However, slot 109 is too narrow to permit button 108 or the body of rod 58 distal to shank 110 to pass therethough.

As shown in FIG. 5 and 6, plate 106 is provided with a pair of safety arcs 107 which are positioned to make contact with drive head 92. Only one safety arc 107 is visible, the other being hidden in these figures. Cutter drive plate 106 is operable between a proximal position, as shown in FIG. 5 and a distal position, as shown in FIG. 6. When plate 106 is in its proximal position, corresponding to the retracted position for cutter 34, safety arcs 107 will be in contact with drive head 92, if the head is in its proximal position corresponding to the jaws open position. Thus, plate 106 cannot be moved distally so as to advance the cutter. However, when actuator handle 24 is drawn to the jaws closed position, as shown in FIG. 6, plate 106 can be moved distally, thus advancing cutter 34. This arrangement prevents the inadvertent laceration of tissue which might occur if the cutter 34 could be advanced when the jaws are open.

Spring 116 has several parts, ratchet control portion 122 having been mentioned above. Spring 116 also includes a cutter biasing section 118 which, as shown in FIGS. 4, 5 and 6 serve to urge plate 106 proximally. Thus, when the surgeon releases the distal pressure on ear 28, the cutter 34 will be retracted. Spring 116 is captured within suitable recesses formed into the right and left sides of housing 14 so as to permit the independent movements of ratchet control portion 122 and blade biasing section 118. Spacer tab 120 of spring 116 is notched out of spring 116 and serves to frictionally fit spring 116 to plate 106 during assembly. Apertures for axle 114 are provided in both sides of housing 14. Thus, during assembly spring 116 is attached to plate 106 as indicated and axle 114 of plate 106 is inserted into its corresponding aperture. In this way, assembly of the instrument is greatly facilitated.

As also shown in FIGS. 4, 5 and 6, rotation knob 32 surrounds sheath 12 and is tightly fitted thereto. Sheath 12 is loosely fitted within housing 14 so that it can be rotated by the surgeon by means of rotation knob 32. When sheath 12 is so rotated, the entire clamping and cutting mechanism will be rotated as well due to the fact that the clamping arms 15, 17, 19 and 21 are secured to sheath 12. As shown in FIG. 3B, sheath 12 is provided with a slot 23 which preferably extends through 270° of the circumference of sheath 12. One side of handle 14 is formed with a pin (not shown) positioned to protrude into slot 23, thus preventing axial movement of sheath 12 while permitting its rotation by means of knob 32.

Figure 8:
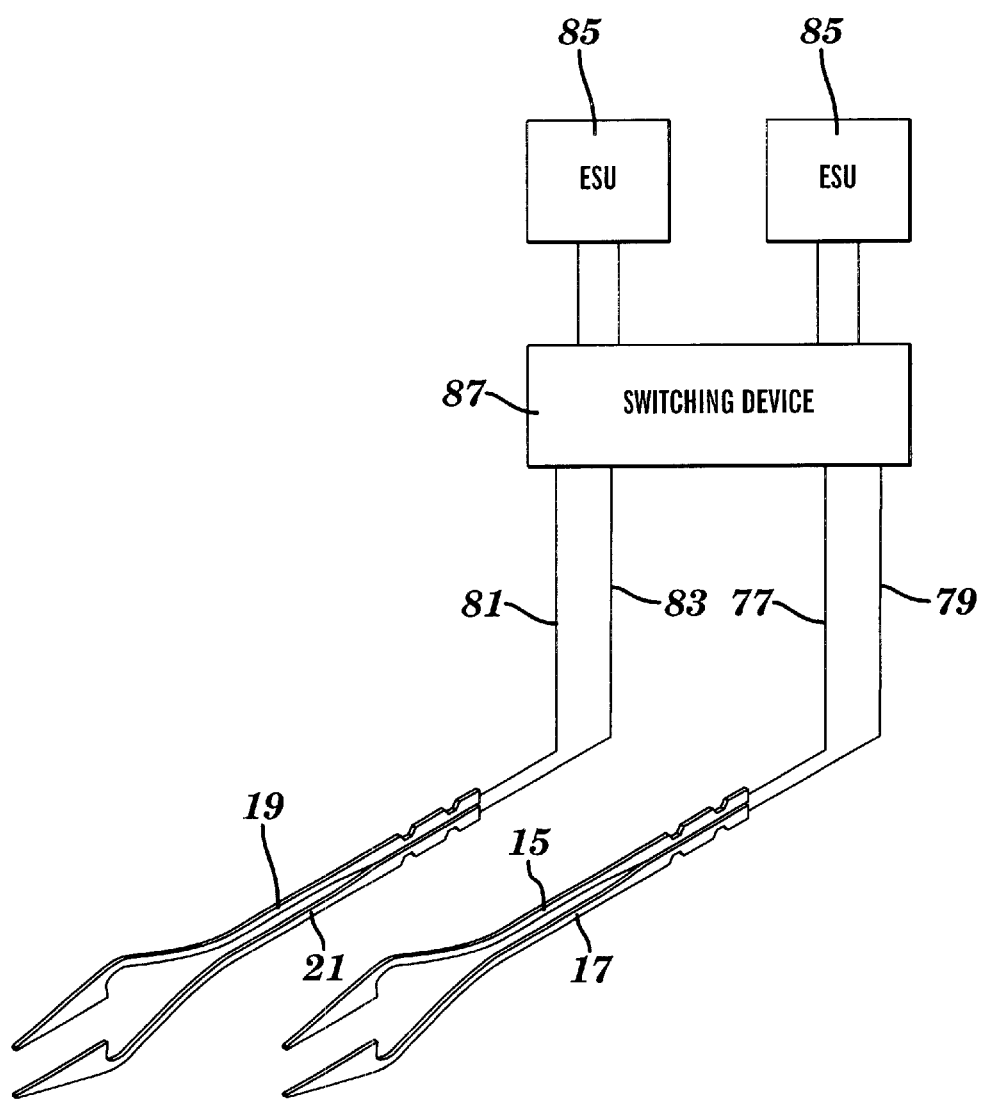
FIG. 8 is a schematic diagram showing a preferred way in which the clamping arms of the invention can be energized for electrosurgical use.

As shown in FIG. 8, clamping arms 15, 17, 19 and 21 may be connected by wires 77, 79, 81 and 83, respectively to one or more electrosurgical units 85. These connections can be made through a switching device 87. Such an arrangement permits the clamping arms and their associated jaws to be energized with different polarity patterns. For example, arms 15 and 19 can be of positive polarity while arms 17 and 21 can be negative. If arms 15 and 17 are energized by one ESU while arms 19 and 21 are energized by a separate ESU, then the resulting heat generated in tissue captured between the jaws will occur primarily between those pairs of arms. On the other hand, if arm 15 and arm 21 were to be connected to one ESU while arms 19 and 17 were to be connected to a separate ESU, then a "cross-fire" pattern of heating would occur. In that pattern, coagulating heat would be generated between arms 19 and 17 and separately between arms 15 and 21, thus creating an "X" pattern in which the greatest amount of heat would occur in the middle. Another possibility would be to connect arms 15 and 19 to the poles of one ESU while arm 17 and 21 would be connected to the poles of a separate ESU. In this configuration, coagulating heat would be generated primarily between arms 15 and 19 on the one hand and arms 17 and 21 on the other. These various firing arrangements can be accomplished using technology well known to those skilled in the art. Furthermore, those skilled in the art will appreciate that the same firing patterns can be accomplished using a single ESU with appropriate signal splitting and switching devices.

An advantage of the above-described instrument concerns the range of motion of its jaws with relation to the diameter of sheath 12. Clamping arms 15 and 17 are configured so that upon closure, they meet first at their wrists 55 and 57. Similarly, arms 19 and 21 meet at wrists 59 and 62, thus creating a relatively short cantilever beam from the wrists to the distal tips of the clamping arms. This arrangement, in turn, permits the ramps 61, 63 and 64, 65 to diverge distally at a greater angle than would be possible if the arms were to meet first at their tips. Thus, the described arrangement permits a wider jaw opening for a given sheath diameter. This advantage is maximized with the use of ramp notches 90 which are provided in the distal end 11 of sheath 12. The distal end 11 of sheath 12 is positioned proximally adjacent to the heels 82, 84, 86 and 88, thus serving as a tissue stop to prevent tissue from contacting the cutting edge 91 of cutter 34 when cutter 34 is retracted.

Those skilled in the art will appreciate that various modifications can be made to the above-described embodiment of the subject invention without departing from its essence. It is intended to encompass all such modifications within the scope of the following appended claims.

What is claimed is:

1. An endoscopic grasping tool surgical instrument comprising:

a tubular sheath having a proximal end and a distal end;

a handle mounted on the proximal end of the sheath and having a jaw actuator operable between a jaws open position and a jaws closed position;

at least one pair of clamping arms having proximal ends, said arms being anchored at their proximal ends to the sheath and being disposed in opposed relation to each other partially within the sheath, each arm having a jaw protruding from the distal end of the sheath, each jaw having a distal tip and a heel proximally separated from the tip by a tissue grasping surface and each arm having a wrist proximally separated from its associated jaw by a ramp, each ramp being disposed in distally diverging relation to its counterpart ramp and each arm having a substantially straight portion proximal to its wrist, each pair of arms being movable relative to one another between an open position in which the wrists and jaws are spaced apart and a closed position in which the wrists and jaws meet; and a drive chassis disposed within the sheath and extending proximally into the handle and having a proximal end positioned adjacent the actuator so as to be driven distally as the actuator is operated from its jaws open position to its jaws closed position, the drive chassis having camming surfaces at its distal end which engage the ramps of the clamping arms so as to urge the arms together as the chassis moves distally, the arms being so configured that, as they are urged together, they meet first at their wrists, then at their distal tips and lastly at their heels.

2. The instrument of claim 1 wherein the arms are electrically conductive and electrically isolated from one another and wherein at least one of each pair is individually connectable to an electrosurgical generator.

3. The instrument of claim 2 in which there are two pairs of clamping arms in a parallel and spaced apart relationship with one another in further combination with a surgical cutter disposed between the pairs of arms and supported for reciprocating longitudinal movement between an advanced position in which the cutter occupies at least part of an envelope of space defined by and between the two pairs of jaws and a retracted position in which the cutter is in a position proximal to the jaws.

4. The instrument of claim 1, 2 or 3 in which the actuator is comprised of a drive head located proximally adjacent to the drive chassis, which drive head moves distally as the actuator is operated from its jaws open position to its jaws closed position.

5. The instrument of claim 4 in combination with means for preventing movement of the drive head proximally following its movement distally.

6. The instrument of claim 5 in which the preventing means is a ratchet comprised of a series of teeth formed on the drive head and a pawl mounted in the handle for engaging the teeth.

7. The instrument of claim 3 in which the cutter has a cutting edge and the cutter is so shaped that no portion of the edge protrudes outside the envelope of space when the cutter is in its advanced position.

8. The instrument of claim 3 in which the actuator is comprised of a drive head located proximally adjacent the drive chassis, which drive head moves distally as the actuator is operated from its jaws open position to its jaws closed position and in which the cutter is attached to a drive rod disposed within the sheath for reciprocating longitudinal movement therein and the drive rod is operatively coupled to a drive plate, said plate being disposed proximally adjacent the drive head and movable between a cutter advanced position and a cutter retracted position, the location and configuration of the drive plate being such that its movement to the advanced position is blocked by the drive head when the drive head is not in its jaws closed position.

9. An endoscopic grasping tool surgical instrument comprising:
   a tubular sheath having a proximal end and a distal end;
   a handle mounted on the proximal end of the sheath and having a drive head operable between a jaws open position and a jaws closed position;
   at least one pair of clamping arms disposed in opposed relation to each other partially within the sheath, each arm having a jaw protruding from the distal end of the sheath, and each pair of arms being movable relative to one another between an open position in which the jaws are spaced apart and a closed position in which the jaws meet;
   a drive chassis disposed within the sheath and extending proximally into the handle and having a proximal end positioned adjacent the head so as to be driven distally as the head is operated from its jaws open position to its jaws closed position, the drive chassis being operably coupled to the clamping arms so as to move the jaws together as the chassis moves distally; and
   a ratchet for preventing movement of the head proximally after it has moved distally, the ratchet comprising a series of teeth formed on the head and a pawl mounted on the handle for engaging the teeth.

10. An endoscopic grasping tool surgical instrument comprising:
    a tubular sheath having a proximal end and a distal end;
    a handle mounted on the proximal end of the sheath and having a drive head operable between a jaws open position and a jaws closed position;
    two pairs of clamping arms, the arms of each pair being disposed in opposed relation to each other partially within the sheath and the two pairs being in a spaced apart, parallel relationship with one another, each arm having a jaw protruding from the distal end of the sheath and each pair of arms being movable relative to one another between an open position in which the jaws are spaced apart and a closed position in which the jaws meet;
    a drive chassis disposed within the sheath and extending proximally into the handle and having a proximal end positioned adjacent the head so as to be driven distally as the head is operated from its jaws open position to its jaws closed position, the drive chassis being operably associated with the clamping arms so as to move the jaws together as the chassis moves distally;
    a surgical cutter disposed between the pairs of arms and supported for reciprocating longitudinal movement between an advanced position in which the cutter occupies at least part of an envelope of space defined by and between the two pairs of jaws and a retracted position in which the cutter is proximal to the envelope;
    a drive rod disposed within the sheath having a distal end operatively coupled to the cutter and a proximal end in the handle;
    a drive plate operatively coupled to the distal end of the drive rod, said plate movable distally to a cutter advanced position and proximally to a cutter retracted position, said plate being disposed proximally adjacent the head so as to be blocked in its movement to the cutter advanced position when the head is not in its jaws closed position.

11. The instrument of claim 10 wherein the cutter has a cutting edge and the cutter is so shaped that no part of the edge protrudes outside the envelope when the cutter is in its advanced position.

12. An endoscopic grasping tool surgical instrument comprising:
    a tubular sheath having a proximal end and a distal end;
    two pairs of clamping arms, the arms of each pair being disposed partially within the sheath in opposed, normally open relationship to each other and the two pairs being in a spaced-apart, parallel relationship with each other, each arm having a jaw protruding from the distal end of the sheath and each pair of arms having camming ramps and being movable relative to one another between an open position in which the jaws are spaced apart and a closed position in which the jaws meet;
    a drive chassis disposed within the sheath and supported for reciprocating axial movement within the sheath, said drive chassis having camming surfaces for engaging the ramps so as to cause movement of the arms as the chassis moves axially, said camming surfaces including at least one lug positioned to maintain separation of corresponding arms during their movement; and
    an actuator handle mounted on the proximal end of the sheath and operably associated with the drive chassis for causing axial movement thereof.

* * * * *